United States Patent [19]

Hall

[11] Patent Number: 5,786,163
[45] Date of Patent: Jul. 28, 1998

[54] BNP ANTIBODY AND IMMUNOASSAY USING IT

[75] Inventor: Christian Hall, Snarøya, Norway

[73] Assignee: Medinnova SF, Oslo, Norway

[21] Appl. No.: 338,558

[22] PCT Filed: Jun. 2, 1993

[86] PCT No.: PCT/GB93/01173

§ 371 Date: Nov. 21, 1994

§ 102(e) Date: Nov. 21, 1994

[87] PCT Pub. No.: WO93/24531

PCT Pub. Date: Dec. 9, 1993

[30] Foreign Application Priority Data

Jun. 3, 1992 [GB] United Kingdom ............ 9211686

[51] Int. Cl.$^6$ ............................................. G01N 33/53
[52] U.S. Cl. ..................... 435/7.92; 435/7.93; 435/7.94; 435/7.95; 435/975; 435/518; 530/387.9; 530/388.1; 530/388.24
[58] Field of Search ............................ 435/7.1, 7.9, 7.92, 435/7.93, 7.94, 7.95, 975; 436/518, 524, 528, 530, 534; 530/403, 399, 402, 810, 812, 811, 387.9, 388.1, 388.24, 389.1, 389.2

[56] References Cited

FOREIGN PATENT DOCUMENTS 0385476  9/1990  European Pat. Off. .

OTHER PUBLICATIONS

Japanese Patent Abstract No. 92–053618.
Chemical Abstract No. 114: 240736K.
Mukoyama et al., J. Clin. Invest. 87(4): 1402–1412, 1991.
Sudoh et al., Nature 332:78–81, 1988.
Sudoh et al., BBRC 159: 1427–1434, 1989.
Staros et al., Analyt. Biochem. 156: 220–222, 1986.
Chemical Abstract No. 116(19): 192485v.
Chemical Abstract No. 115(17): 174663b.
Chemical Abstract No. 115(5): 43473s.
Chemical Abstract No. 114(17): 158509.
Sherry et al., Biochem Biophys Res. Comm. 173(3):1072–1078, Dec. 31, 1990.
Jue et al. Biochemistry, 29:8371–8377, 1990.
Cseh et al. Journal of Biological Chemistry. 264(27):16256–16260, 1989.
Kriegler et al. Cell, 53:45–53, 1988.
Voiler et al in "Alternative Immunoassays" Collins et al. eds., 1985 by John Wiley and Sons Ltd. pp. 77–86.
Hino et al. Biochemical and Biophysical Research Communications, 167(2):693–700, 1990.
Mukoyama et al, Journal of Clinical Investigation, 87(4):1402–1412 Apr. 1991.

*Primary Examiner*—Paula K. Hutzell
*Assistant Examiner*—Patricia A. Duffy
*Attorney, Agent, or Firm*—Pennie & Edmonds

[57] ABSTRACT

The present invention provides antibodies for use in a method of immunoassay being antibodies specific to the polypeptide consisting of amino acids 1–76 (SEQ ID NO:1) of N-terminal brain natriuretic factor BNP(1–76). Also provided are methods and kits for the diagnosis or prognosis of conditions in which BNP(1–76) is a diagnostic or prognostic indicator, such as heart failure or hypervolemia.

13 Claims, 1 Drawing Sheet

BNP ANTIBODY AND IMMUNOASSAY USING IT

This invention relates to the N-terminal section of Brain Natriuretic Peptide Prohormone, BNP(1-76)(SEQ ID NO:1) and the use of antibodies against this in immunoassays in biological fluids for the purpose of biological research and medical diagnosis, for example of heart failure or hypervolaemia.

Heart failure is a common clinical syndrome especially among elderly people. Population surveys indicate that the condition affects about 2% of the total population in the western world. The syndrome usually presents itself with an insidious onset with unspecific symptoms such as dyspnea on exertion, fatigue and peripheral oedemas. To establish the diagnosis the physician usually must either rely on his clinical experience or refer the patient to a cardiological center for echocardiography, radionuclide scanning, exercise testing or catheterization.

Heart disease represents a significant drain on health resources in many major countries, and whilst an early diagnosis may help in controlling the condition and preventing rapid progression to severe heart failure, it would obviously be preferable to be able to identify those patients in which heart failure is likely to occur before it actually does so, ie. to prognose rather than diagnose.

Unfortunately, there are at present no completely satisfactory methods for predicting the likelihood of heart failure. Problems frequently observed with such methods are insufficient accuracy and sensitivity, and the disadvantages of the necessity for expensive equipment requiring specially trained personnel (eg. in echocardiography). A need therefore exists for a simple method of accurately and sensitively, not only diagnosing, but also predicting the likelihood of onset of heart failure.

Whilst heart failure can be defined as a symptomatic state ie. an overt disease or syndrome, patients may frequently pass through a state of asymptomatic cardiac dysfunction ie. a sub-clinical condition without overt symptoms, before heart failure manifests itself. However, we have now found that not all patients having cardiac dysfunction go on to develop severe heart failure, and that the risk of heart failure for some such people is much greater than for others. To be able to identify those people at particular risk of developing heart failure in order that they may be caught and treated before heart failure occurs would be of great clinical importance; at the moment existing treatments eg. ACE inhibitors are very expensive and it is not cost-effective for everyone to be treated to try to prevent the onset of heart failure.

Brain Natriuretic Peptide (BNP) is a polypeptide originally isolated from porcine brain by T. Sudoh and coworkers (Nature 1988; 332: 78-81). After cloning and sequence analysis of CDNA coding for the peptide (T. Sudoh BBRC 1989; 159: 1427-34) human BNP was shown to be produced in the human heart. Human Brain Natriuretic Peptide is believed to be produced in cardiac myocytes as a prohormone (proBNP or BNP(1-108)). proBNP consists of 108 amino acids and is split, before or during secretion, at amino acids Arg76—Ser77 into BNP and the N-terminal part of the prohormone, BNP(1-76)(SEQ ID NO:1), that is the peptide consisting of the first 76 amino acids from the N-terminal of proBNP.

The BNP(77-108) plasma concentration is increased in patients suffering from heart disease leading to heart failure. The cardiac monocytes secrete another factor, namely atrial natriuretic factor (ANF) but the secretory response to heart failure or incipient heart failure seems to be much larger in the BNP system compared to the ANF system (Mukoyama et al. J Clin Invest 1991; 87: 1402-12).

The present invention is based on the concept that human BNP(1-76)(SEQ ID NO:1), due to a long half-life as compared with BNP hormone itself and high initial concentration, is a particularly good diagnostic indicator or predictor of heart disease and also of hypervolaemia.

Human BNP(1-76)(SEQ ID NO:1) may thus be used to provide the basis of either a diagnostic or a prognostic test for heart failure, primarily in the biosynthesis of antibodies for use in such a test but also as competing antigen in competitive binding immunoassays. For such use in making antibodies BNP(1-76)(SEQ ID NO:1) or an antigenic fragment thereof may advantageously be conjugated to an immunogenic protein or peptide such as PPD, a protein derivative of tuberculin, Keyhole Limpet Haemocyanin or bovine serum albumin.

Thus human BNP(1-76)(SEQ ID NO:1) or an antigenic fragment thereof or polypeptide extension thereof lacking BNP activity and having at least one antigenic epitope of human BNP(1-76)(SEQ ID NO:1), conjugated to one or more immunogenic polypeptides, constitutes one aspect of the present invention; these polypeptides may be used to make either polyclonal or monoclonal antibodies specific to BNP(1-76)(SEQ ID NO:1). Such monoclonal and polyclonal antibodies constitute two further aspects of the invention.

According to a still further aspect of the invention we provide a method of immunoassay for human BNP(1-76) (SEQ ID NO:1) or an antigenic fragment thereof or polypeptide extension thereof lacking BNP activity wherein the primary binding partner therefor is a monoclonal or polyclonal antibody according to the invention. Methods of immunoassay are of course well known in the art eg. RIA, ELISA, fluorescence immunoassay (FIA) or dry chemistry test strip immunoassays. Such an immunoassay will, in general, use a monoclonal or polyclonal antibody according to the invention in immobilised form, e.g. on microtitre plates, membranes or beads, to isolate the target BNP(1-76) compound. In a sandwich assay, the bound antigen may be labelled using additional soluble antibody according to the invention, which may be monoclonal or polyclonal and which may either carry a label or, more conveniently, may itself be labelled subsequently by reaction with a secondary antibody carrying a label.

Thus, if the primary antibody according to the invention is raised in mice or rabbits, the labelled secondary antibody may be an anti-mouse or anti-rabbit antibody.

Suitable labels include radionucleides, fluorescent substances eg. europium based fluorogens, enzymes, for example as used in ELISA systems employing automated hybrid methods or dyes or coloured particles such as colloidal gold.

Alternatively, a competitive binding assay may be used, wherein a known quantity of labelled human BNP(1-76) (SEQ ID NO:1), or antigenic fragment or inactive extension thereof, is added to the analyte solution and contacted with a limited quantity of the immobilised monoclonal or polyclonal antibody, whereby the amount of labelled antigen which is immobilised is inversely proportional to the amount of target antigen present in the analyte.

The invention thus extends to labelled forms of human BNP(1-76)(SEQ ID NO:1) or antigenic fragments or polypeptide extensions thereof lacking BNP activity and to labelled forms of the antibodies of the invention.

The invention also comprises a kit for immunoassay of human BNP(1-76)(SEQ ID NO:1) or an antigenic fragment or polypeptide extension thereof lacking BNP activity comprising:

(a) a monoclonal or polyclonal antibody according to the invention in immobilised form and, at least one further component selected from;

(b) a labelled sample of BNP(1-76)(SEQ ID NO:1) or an antigenic fragment or polypeptide extension thereof lacking BNP activity;

(c) said monoclonal or polyclonal antibody in non-immobilised form;

(d) a labelled secondary antibody specific to said antibody (c).

Such an immunoassay and kit may be used in research into related biological systems as well as for diagnosis or prognosis of conditions wherein the human BNP(1-76) (SEQ ID NO:1) level in body fluids is a diagnostic or predictive indicator.

The invention also comprises a method of diagnosis or prognosis of a condition in which the concentration of human BNP(1-76)(SEQ ID NO:1) or an antigenic fragment or polypeptide extension thereof lacking BNP activity is a diagnostic or predictive indicator, wherein a body fluid of a patient is subjected in vitro to immunoassay to detect or assay the presence or quantity therein of human BNP(1-76) (SEQ ID NO:1).

We have recently found that another natriuretic factor namely pro-ANF, and in particular N-terminal pro-ANF, can serve as an indicator of risk of heart failure in patients lacking overt symptoms of heart failure. The level of pro-ANF in body fluids can be directly related to the risk of heart failure, predominantly related to increased atrial pressure. In contrast, BNP(1-76)(SEQ ID NO:1) is predominantly an indication of a heart condition related to increased ventricular pressure. Human BNP(1-76)(SEQ ID NO:1) as an antigenic fragment or inactive polypeptide extension thereof can also be used to assess risk of heart failure in addition to its use in diagnosis of actual heart failure. Furthermore, assay of both N-terminal pro-ANF and BNP(1-76)(SEQ ID NO:1) in body fluids can assist in determining whether atrial or ventricular pressure is concerned.

Thus, the immunoassay can be used in the monitoring of heart failure treatment. Such treatment is aimed at reducing the hypervolemia and excessive vasoconstriction seen in heart failure by the administration of diuretics and vasodilators. By decreasing the pressure in the cardiac chambers such treatment will lower cardiac production of BNP(1-76) (SEQ ID NO:1). The resultant decrease in plasma BNP (1-76) concentration serve to inform the physician of a significant drug effect. On the contrary, an increase in plasma BNP(1-76) indicates that an adjustment of dosage might be necessary.

Although less well documented at this time human BNP(1-76)(SEQ ID NO:1) may also be used as a diagnostic tool in the diagnosis of hypervolemia without heart failure. The immunoassay therefore has potential use also in the inhospital intensive care setting where monitoring of volume status is essential.

The body fluid on which the immunoassay is performed may be any body fluid in which the human BNP(1-76)(SEQ ID NO:1) is located, but conveniently will be plasma or serum. In some cases it may be convenient to extract the peptide, or otherwise treat the sample prior to assay.

The human BNP(1-76)(SEQ ID NO:1) peptide or an antigenic or immunogenic fragment thereof may be produced by synthesis from its constituent amino acids or by assembly of pre-synthesised blocks of amino acids using techniques well known in the art. Where labelled material is required, the label may be introduced by standard techniques.

For the purpose of raising monoclonal or polyclonal antibodies, the human BNP(1-76)(SEQ ID NO:1) or antigenic fragment thereof may be conjugated to an immunogenic protein or peptide, for example PPD, a protein derivative of tuberculin, eg. using 1-ethyl-3-(3-dimethylaminopropyl)carbodiimide according to the method of Staros et al (Analyte Biochem 1986; 156: 220–222).

The antibodies of the invention may be made by injecting a host animal, eg. a mouse or rabbit, with the BNP antigen of the invention, advantageously a conjugate with an immunogenic protein as described above, to provide either a serum containing polyclonal antibodies or spleen cells for conversion to hybridomas or immortalised cell lines producing monoclonal antibodies.

BRIEF DESCRIPTION OF THE DRAWINGS

The following Examples are given by way of illustration only with reference to the accompanying drawing in which.

EXAMPLE 1

Figure 1:
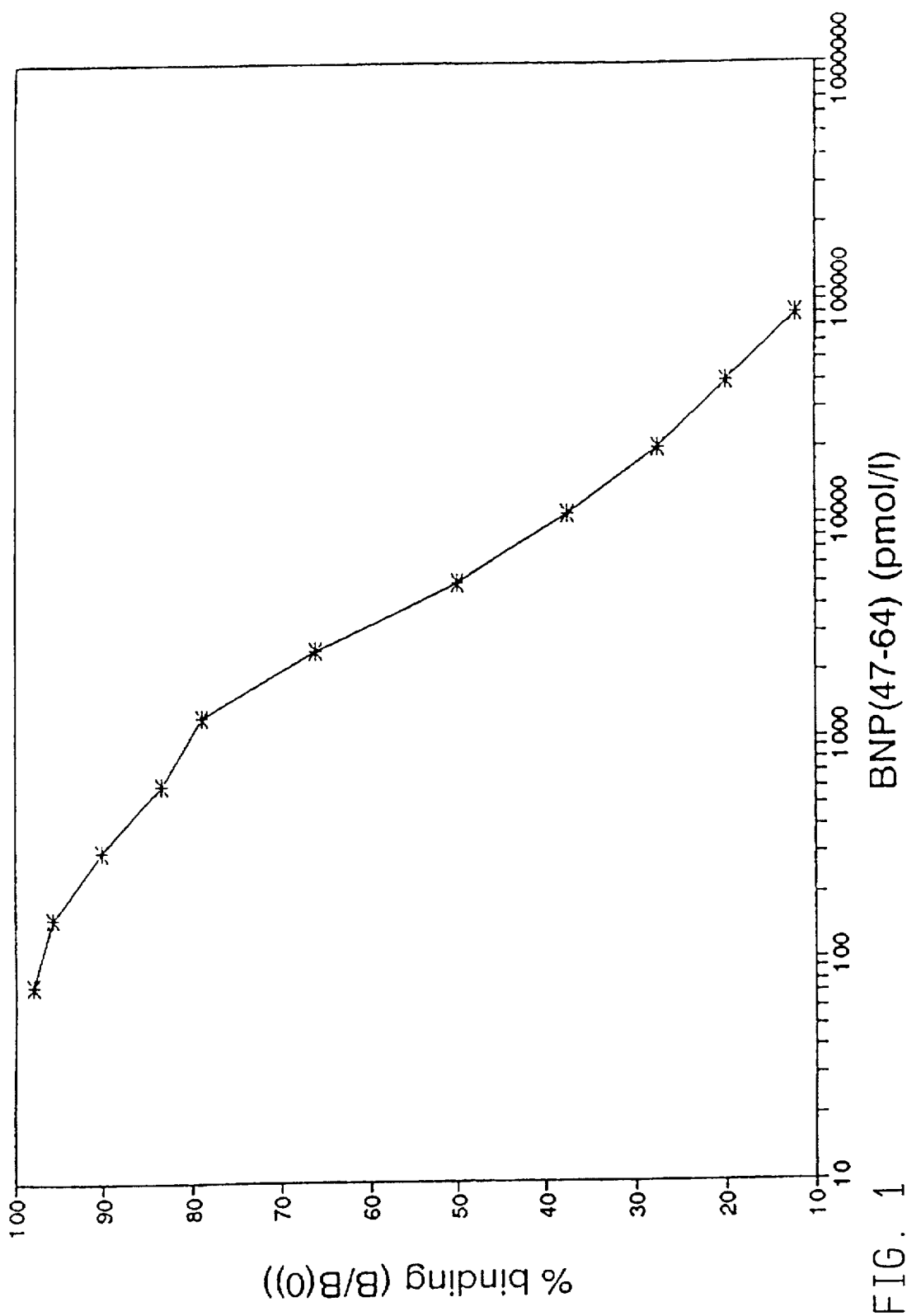
FIG. 1 shows a standard curve for immunoassay for BNP(1-76) using synthetic BNP(47-64) as immunogen, standard and tracer, and polyclonal rabbit antibody. (Abscissa shows BNP(47-64) pmol/l; ordinate shows % binding (B/B(O))).

Production of Monoclonal Antibody Against BNP (1-76)

1) Conjugation

Three synthesized fragments of BNP(1-76)(SEQ ID NO:1): BNP(1-21), BNP(22-46) and BNP(47-64) were acquired from Peninsula laboratories and conjugated to PPD (protein derivative of tuberculin) according to Staros et al (Analyt Biochem 1986; 156: 220–222).

2) Immunization

Balb C mice, preimmunized with BCG antigen were utilized. The mice received a 50 microgram mixture of the three conjugates in 200 μl of Freunds incomplete adjuvant. The mixture was given in 2×200 μl injections on 2 occasions 2 weeks apart. 2 weeks after the last injection 50 μg of conjugate mixture in saline was injected intraperitoneally.

3) Fusion 3 days after intraperitoneal immunization mouse splenic cells were fused with SP 2/0 myeloma cells and the resultant hybridomas selected in HAT medium. The suspension of hybridomas was distributed in 960 wells in Dulbeccos medium enriched with 10% human endothelial cell supernatant.

4) Screening

Method 1

Costar microtiter plates were coated with a mixture of the synthetic BNP peptide sequences (0.5 μg/ml). Supernatants were then added and binding of antibody from supernatants was screened by ELISA through the addition of anti mouse IgG conjugated to horseradish peroxidase enzyme followed by substrate solution (OPD).

Method 2

An alternative method of screening is to coat Greiner microtiter plates with goat anti mouse IgG (1.0 μg/ml). Supernatants are then added and incubated. Biotinylated synthetic BNP peptide sequences are added and the ability of supernatants to bind peptide are screened by ELISA through the addition of streptavidin-conjugated horseradish peroxidase enzyme followed by substrate solution (OPD).

5) Cloning

Hybridomas producing antibodies to the peptide mixture were cloned and subcloned in two runs. Clone 1C7 was shown to react with peptide sequence BNP(47–64). This clone was grown and the supernatant utilised in immunoassay for BNP(1–76).

EXAMPLE 2

Immunoassay for BNP(1–76)(SEQ ID NO:1)

The 1C7 antibody can be utilised in various types of immunoassays for BNP(1–76)(SEQ ID NO:1). These include a) Radioimmunoassay (RIA)

b) Europium Fluorescence immunoassays (FIA)

c) Enzyme linked immunosorbent assays (ELISA) including automated hybrid methods running on micro titer plates or membranes d) Various dry-chemistry test strip immunoassays The following is an example of a sandwich ELISA.

Costar microtiter plates are precoated with the 1C7 antibody. Sample or standard is added to the wells and after 2 hours of incubation the wells are washed and a secondary antibody (polyclonal or monoclonal) towards BNP(1–76) (SEQ ID NO:1) is added. Again after 2 hours a horseradish peroxidase-labelled anti mouse (rabbit) antibody is supplied and finally after the addition of O-phenylene-diamine substrate the colour is read in a platereader.

EXAMPLE 3

Immunoassay for BNP(1–76) Utilizing Polyclonal Rabbit Antibody

A synthetic peptide subsequence of BNP(1–76)(SEQ ID NO:1), in this case BNP(47–64), was conjugated to PPD according to Staros et al., (Supra). Rabbits were BCG vaccinated and then repeatedly immunized with the conjugated peptide.

Iodination ($^{125}$I) of synthetic BNP(47–64), with a tyrosine group added at the N-terminal end, was done by the chloramine-T method as follows:

Chloramine-T Method 1) 5 μg of the synthetic peptide was reconstituted with 20 μl sodiumphosphate buffer (0.25M, pH 7.5).

2) Approximately 5 μl of $^{125}$-I was added (0.5 mCi).

3) 5 μl of chloramine-T (1 mg/ml) was added and incubated for 45 seconds.

4) 5 μl of sodiummetabisulphite (1 mg/ml) was added and incubated for 45 seconds.

5) The mixture was then fractionated on a column with Sephadex G10.

6) The fractions were counted with a gamma-counter, and the fraction/fractions with highest counts per minute (cpm) were selected as tracer for use in the RIA methods.

Sample or standards (BNP[47–64]), together with tracer (iodinated BNP(47–64)) and polyclonal antibody from rabbit serum, are mixed in polystyrene assay tubes. After 48 hours of incubation at 4° C., normal serum from rabbit, and goat anti-rabbit IgG are added. After 2 hours of incubation, polyethyleneglycol (PEG) is added and the samples are centrifuged. The supernatant is removed and the counts per minute (cpm) in precipitate are measured with a gamma-counter. An example of a standard curve obtained by this type of assay is shown in FIG. 1.

---

I claim:

1. An antibody composition comprising an antibody which specifically binds to a polypeptide consisting of amino acids 1–76 of the N-terminal of human pro-brain natriuretic factor (BNP(1–76)(SEQ ID NO:1)).

2. The antibody composition as claimed in claim 1 which comprises a monoclonal antibody.

3. The antibody composition as claimed in claim 1 which comprises a polyclonal antibody.

4. The antibody composition as claimed in claim 1 carrying a label.

5. The antibody composition as claimed in claim 4 in which the label is a radionuclide, a fluorescent substance, an enzyme, a dye or coloured particles.

6. The antibody composition of claim 1, wherein the antibody is immobilized on a solid support.

7. A method of immunoassay for BNP(1–76), (SEQ ID NO:1), which comprises:
   (a) contacting a body fluid from a patient with a primary antibody according to claim 1 to form a primary antibody-BNP(1–76)(SEQ IS NO:1) complex; and
   (b) detecting the formation of said complex.

8. The method as claimed in claim 7 in which the primary antibody is immobilized on microtitre plates, membranes or beads.

9. The method as claimed in claim 8 in which said detecting comprises contacting said complex with a second antibody which binds BNP(1–76)(SEQ ID NO:1) to form a second complex comprising a primary antibody-BNP(1–76)(SEQ ID NO:1)-secondary antibody and detecting the formation of said second complex to provide a sandwich assay.

10. The method as claimed in claim 7 wherein said primary antibody is immobilized and wherein said contacting comprises first adding a known quantity of labelled human BNP(1–76)(SEQ ID NO:1) or a labelled antigenic fragment thereof to the body fluid in solution to provide a competitive binding assay.

11. A labelled human BNP(1–76)(SEQ ID NO:1) or a labelled antigenic fragment thereof.

12. A kit for immunoassay of human BNP(1–76)(SEQ ID NO:1) lacking BNP activity comprising:
   (a) an antibody according to claim 1 in immobilized form and, at least one further component selected from the group consisting of:
   (b) a labelled sample of human BNP(1–76)(SEQ ID NO:1) or an antigenic fragment thereof lacking BNP activity;
   (c) an antibody according to claim 1; and
   (d) a labelled secondary antibody which specifically binds to an antibody according to claim 1.

13. An in vitro method of diagnosis or prognosis of heart disease comprising:
   (a) contacting a body fluid from a patient with a primary antibody according to claim 1 to form a primary antibody-BNP(1–76)(SEQ IS NO:1) complex; and
   (b) detecting the formation of said complex to determine the level of BNP(1–76)(SEQ ID NO:1) in the body fluid wherein an increased level of BNP(1–76)(SEQ ID NO:1) as compared to normal individuals is indicative of a diagnosis or prognosis of heart disease.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 76 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:1:

```
His Pro Leu Gly Ser Pro Gly Ser Ala Ser Asp Leu Glu Thr Ser Gly
 1               5                  10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg
65                  70                  75
```